United States Patent [19]
Lipps et al.

[11] Patent Number: 5,565,431
[45] Date of Patent: Oct. 15, 1996

[54] CANCER CELL INHIBITORS AND METHOD

[76] Inventors: Binie V. Lipps; Frederick W. Lipps, both of 4509 Mimosa Dr., Bellaire, Tex. 77401

[21] Appl. No.: 310,341

[22] Filed: Sep. 22, 1994

Related U.S. Application Data

[63] Continuation-in-part of Ser. No. 262,678, Jun. 20, 1994.
[51] Int. Cl.$^6$ .............................. A61K 38/17; C07K 14/46
[52] U.S. Cl. ............................ 514/21; 530/300; 530/350; 530/856
[58] Field of Search ...................................... 530/344, 416, 530/326, 300, 350, 395, 856; 514/2, 8, 14, 21; 424/542

[56] References Cited

U.S. PATENT DOCUMENTS

| | | | |
|---|---|---|---|
| 3,888,977 | 6/1975 | Sanders | 424/542 |
| 4,672,107 | 6/1987 | Kilmon | 530/350 |
| 4,774,318 | 9/1988 | Marquardt et al. | 930/10 |

OTHER PUBLICATIONS

Anticancer Research, vol. 10, issued 1990, Field et al, pp. 1–22.
Science, vol. 249, issued 1990, Hussein et al, pp. 1564–1566.
Biochem. Biophys. Acta, vol. 136, issued 1967, Braganca et al, "Isolation and Properties of a Cobravenom Factor . . . ", pp. 508–520.
Life Sciences, vol. 40, No. 16, issued 1987, issued Chaim-Matyas et al, "Cytotoxic Activity of Various Snake Venoms . . . ", pp. 1601–1607.
Oncogene, vol. 6, issued 1991, Garcia et al, pp. 1983–1989.
S. Afr. J. Chem., vol. 34, No. 4, issued 1981, Joubert, "Primary structure and properties of toxin CM–16 . . . ", pp. 128–131.
Chemical Abstracts vol. 105:165008h (1986).
Biochem. Biophys. Res. Chem., vol. 201, No. 3, issued 30 Jun. 1994, Hung et al, "Isolation of Multiple Isoforms . . . ", pp. 1414–1423.
Thrombosis Research, vol. 58, issued 1990, Nakagaki et al, "Isolation and Characterization of a Protein C . . . ", pp. 593–602.
Toxicon, vol. 27, No. 2, issued 1989, Martinez et al, "Antigenic Relationships of Fractionated Western Diamondback . . . ", pp. 239–245.

*Primary Examiner*—Jeffrey E. Russel
*Attorney, Agent, or Firm*—John R. Casperson

[57] ABSTRACT

Novel cancer cell inhibitors have been isolated from the venoms of poisonous snakes *Crotalus atrox* and *Naja n. kaouthia*; they are called Atroporin and Kaotree, respectively. The cancer cell inhibitors Atroporin and Kaotree are characterized as potent anti cancer agents. Atroporin and Kaotree, individually, or combined together selectively kill various types of cancer cells in concentrations as low as 0.5 μg/ml. Atroporin and Kaotree are characterized as stable protein components of venoms consisting of peptides whose molecular weights are approximately 35,000 and 6,000 daltons, revealed by gel electrophoresis. The partial sequence of Atroporin for its first fifteen N-terminal amino acids is:

SEQ ID: 1 =[Val, Ile]-[Val, Ile]-Gly-Gly-Asp-Glu-(Cys)-Asn-Ile- Asn- Glu-His-Arg-Ser-Leu and, similarly for Kaotree:

SEQ ID: 2=Met-Glu-Cys-Tyr-Arg-Met-Ser-Asn-Ile-Val- Thr-Cys-Gln-Pro-Trp.

Neither of these sequences appear in standard data bases including all known proteins, therefore they are novel proteins. Atroporin and Kaotree have cytolytic, i.e. killing effect, on various types of cancer cells and are claimed as versatile anti cancer agents. Furthermore, Atroporin and Kaotree are claimed as therapeutic agents for a wide range of cancers such as: breast, colon, liver, lung pharynx ovary etc. It is also an object of this invention to provide two different embodiments such as Atroporin and Kaotree, or the combination of both, as compositions for the treatment of various types of cancers as a biotherapy.

4 Claims, 11 Drawing Sheets

```
            1  2  3  4  5  6
```

Well no. 1      Markers;     Well no. 4    Markers
Well no. 2,3    Kaotree;     Well no. 5,6  Atroporin

Well no. 1      Markers;      Well no. 4      Markers
Well no. 2,3    Kaotree;      Well no. 5,6    Atroporin

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH:15
( B ) TYPE: AMINO ACID
( C ) STRANDEDNESS: SINGLE
( D ) TOPOLOGY:LINEAR ( i i ) MOLECULE TYPE: PROTEIN IN SEQ ID NO: 1

( i i i ) HYPOTHETICAL: NO ( i v ) ANTI-SENSE: NO ( v ) FRAGMENT TYPE: N ( v i ) ORIGINAL SOURCE: SNAKE VENOM: SEQ ID NO: 1:
    ( A ) ORGANISM: CROTALUS ATRA
    ( B ) STRAIN:WILD
    ( C ) INDIVIDUAL ISOLATE: WESTERN DIAMONDBACK
    ( D ) DEVELOPMENTAL STAGE: ADULT
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE: SNAKE VENOM SEQ ID NO: 1:
    ( A ) LIBRARY:
    ( B ) CLONE:

( i x ) FEATURE:
    ( A ) NAME/KEY:
    ( B ) LOCATION:
    ( C ) IDENTIFICATION METHOD:
    ( D ) OTHER INFORMATION:
        Xaa IN POS 1 IS EITHER Val, OR Ilc.
        Xaa IN POS 2 IS EITHER Val, OR Ilc.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:

( x i ) SEQUENCE DESCRIPTION: SEQ ID NO: 1:

```
Xaa   Xaa   Gly   Gly   Asp   Glu   Cys   Asn   Ilc   Asn
 1                       5                             10

Glu   His   Arg   Ser   Leu
                         15
```

( 2 ) INFORMATION FOR SEQ ID NO: 2:

( i ) SEQUENCE CHARACTERISTICS:
        ( A ) LENGTH: 15
        ( B ) TYPE: AMINO ACID
        ( C ) STRANDEDNESS: SINGLE
        ( D ) TOPOLOGY:LINEAR     ( i i ) MOLECULE TYPE: PROTEIN IN SEQ ID NO: 2

( i i i ) HYPOTHETICAL: NO

( i v ) ANTI-SENSE: NO

( v ) FRAGMENT TYPE: N

( v i ) ORIGINAL SOURCE: SNAKE VENOM: SEQ ID NO: 2:
        ( A ) ORGANISM: NAJA N. KAOUTHIA
        ( B ) STRAIN:WILD
        ( C ) INDIVIDUAL ISOLATE: THAILAND WILD
        ( D ) DEVELOPMENTAL STAGE: ADULT
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: SNAKE VENOM SEQ ID NO: 2:
        ( A ) LIBRARY:
        ( B ) CLONE:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

-continued ( G ) DATE:

( x i ) SEQUENCE DESCRIPTION: SEQ ID NO: 2:

```
Met  Glu  Cys  Tyr  Arg  Met  Ser  Asn  Ile  Val
 1                  5                        10

Thr  Cys  Gln  Pro  Trp
                     15
```

CANCER CELL INHIBITORS AND METHOD

SPECIFICATION

This application is a continuation in part of the application Ser. No. 08/262,678, filed Jun. 20, 1994.

FIELD OF THE INVENTION

The present invention relates to the discovery of two cancer cell inhibitors isolated from the venoms of poisonous snakes *Crotalus atrox* and *Naja n. kaouthia*, which will be referred as Atroporin and Kaotree, respectively. Said compositions of Atroporin and Kaotree consist of a single polypetide moiety having molecular weights approximately 35,000 and 6,000 daltons, respectively. Said compositions are non toxic to normal cells and show regression of ascitic tumors in a mouse model for cancer. Said compositions of Atroporin and Kaotree should be useful as treatments for various human cancers. Clinical trials are being planned.

BACKGROUND OF THE INVENTION

In the prosperous countries, roughly 20%, or one in five will die of cancer. The most frequently occurring cancers worldwide in descending order are: stomach, lung, breast, colon/rectum, cervix and mouth/pharynx. The cytolytic activity of most available anti-tumor chemicals is due to the inhibition of the synthesis and replication of DNA in tumor cells. Surgery, chemotherapy and radiation show limited success, and furthermore, these procedures remove or destroy normal cells along with cancer cells. Therefore, it is of interest to search for new anti-cancer agents having a different mode and site of activity. Moreover, cancer therapy using toxic chemicals give serious adverse side effects and other unpleasant results such as Alopecia (hair loss) which is one of the most distressing one among others.

The search for specific treatments has been vigorously pursued for over a half century, and the use of chemicals to treat cancer continues. The treatment of cancer needs to be changed from chemotherapy to biotherapy using biologicals at much lower dose levels. Monoclonal antibodies alone or coupled with ricin and interferons are the only biologicals until now used for cancer therapy.

Snake venom is a complex mixture of many substances such as toxins, enzymes, growth factors, activators and inhibitors, with wide spectrum of biological activities. For a long time it is believed that snake venom proteins have potential for the treatment of cancer, viral diseases, epilepsy and neurological disorders such as Alzheimer's and Parkinson's diseases etc. A book from CRC press by Kurt F. Stocker entitled "Medical Use of Snake Venom Proteins" reveals the state of the art. Tu and Giltner reported that venoms from the snake families Elapidae, Viperidae and Crotalidae, but not Hydrophidae, caused lysis of Yoshida sarcoma and KB cells. Chaim-Matyas and Ovadia studied the cytotoxic activity of various snake venoms in vitro and in-vivo, using melanoma and chondrosarcoma cells. Braganca et al. were probably first to isolate a factor from cobra venom which is selectively cytotoxic to cancer cells. Subsequently, these investigators isolated the cytotoxic factor having a molecular weight of 10,500 daltons. As recently as 1985, Iwaguchi et al. studied the cytotoxic activity of a cytotoxin isolated from Indian cobra venom against experimental Yoshida tumor cells and observed that the cytolytic activity on tumor cells was far stronger than on exudate cells such as: spleen cells and erythrocytes from rat. Besides, crude snake venoms, purified snake venom proteins have also been reported to have cytolytic activity on KB and Yoshida tumor cells.

Currently, numerous chemicals are being used to treat various types of cancers and such treatment is termed chemotherapy. Chemotherapy is associated with adverse side effects, such as hair loss, diarrhea skin rash, etc., simply because the chemicals used to kill cancer cells also affect normal cells adversely. Chemotherapy requires different chemicals for different types of cancers. The cancer treatment should be changed from chemotherapy to biotherapy using biologicals. Monoclonal antibodies coupled with ricin or other toxins are currently the only biologicals considered for cancer therapy. We strongly believe that snake venom derived Atroporin and Kaotree can play such a biological role by specifically targeting cancer cells.

REFERENCES CITED

U.S. Patent Documents:

| 1. | 3,888,977 | Jun. 19, 1975 | Sanders |
| 2. | 4,672,107 | Jun. 9, 1987 | Kilmon |
| 3. | 4,774,318 | Sep. 27, 1988 | Marquardt et al. |

Other publications:
1. Field, J. K. and Spandidas, D. A.
   Anticancer Research 10: 1–22 (1990)
2. Hussein, A. M., Jimnez, J. J., McCall, C. A. and Yunie, A. A.
   Science 249: 1564–1566 (1990).
3. Stocker, K. F."Medical Use of Snake Venom Proteins" Edited by K. F. Stocker, CRC Press (1990).
4. Tu, A. et al., Research Communications in Chemical Pathology and Pharmacology, vol. 9: 783–786 (1974).
5. Zaheer, A. et al. Cancer Biophys. 5: 41–46 (1980).
6. Braganca, B. M., Patel, N. T. and Badrinath, P. G. Biochemica et Biophysica Acta 136: 508–520 (1967)
7. Chaim-Matyas, A. and Ovadia, M.
   Life Sciences 40: 1601–1607 (1987).
8. Iwaguchi, T., and Hayashi, K. Biochem. Int. 10: 343–349 (1985).
9. Garcia, R., Parikh, N. U., Saya, H. and Gallick G. E. Oncogene 6: 1969–1983 ( 1991).

OBJECTS OF THE INVENTION

It is an object of this invention to claim that the novel compositions of Atroporin and Kaotree can be used to treat various types of cancers, because they show cytolytic activity to a wide range of tumor cells for both in-vitro and in vivo systems. Atroporin and Kaotree and the combination of both inhibit the formation of ascitic tumors in Balb/C mice, which is an in-vivo system. A further object of this invention is to provide a non toxic cancer treatment, without the typical adverse side effects caused by usual chemotherapy. Such a biotherapy will be a major advance in treatment of cancer, will improve the quality of life and shorten recovery time. Furthermore, the combination of Atroporin and Kaotree exhibits enhanced cytolytic activity for certain types of cancers. Hence, it is a further object of the invention to claim that the combination may lead to more effective cancer therapy.

SUMMARY OF THE INVENTION

Cancer cell inhibitors Atroporin and Kaotree have been isolated by fractionating *Crotalus atrox* and *N.n. kaouthia* snake venoms by high pressure liquid chromatography. Each venom resolved into number of major fractions. After testing for the biological activity of all fractions on mouse myeloma cancer (SP/2) cells, the maximum cytolytic activity was revealed in one fraction of each venom. Atroporin and Kaotree are non toxic fractions of their respective snake venoms which are potent anti cancer agents. Atroporin and Kaotree have been isolated from the venoms of *Crotalus atrox* and *Naja n. kaouthia*. Such anticancer proteins may be obtained from venoms of other species of poisonous snakes.

Concentrations of 5 µg/ml down to 0.1 µg/ml of Atroporin or Kaotree kill various types of human cancer cells such as: breast, colon, liver and ovary in-vitro within 24 hours, whereas the said cancer cell inhibitors have no effect on normal mouse: kidney, liver, spleen and erythrocytes in concentrations as high as 5.0 µg/ml. Cancer cell inhibitors Atroporin and Kaotree consist of peptides having molecular weights 35,000 and 6,000 daltons, respectively. Based on cell culture findings and mouse experiments we suggest the following strategy for use in human treatment. Depending upon the cancerous state of the patient, an equal combination of Atroporin and Kaotree consisting of 200 µg/ml should be administered intravenously or by direct perfusion, as follows:

| Day 1 | 200 µg | 1 ml |
| Day 2 | 400 µg | 2 ml |
| Day 3 | 400 µg | 2 ml |

Thus, the first set of treatments will consist of 1 mg in total. This quantity is low in comparison to current chemotherapy practice. Our experience tells us that by our unique methodology venom derived proteins are more biologically active than obtained by other methods. For safety, the following tests to be performed before the first set of treatments and again one month after.

(1) Total white blood cell count (2) Total platelet count

We believe that 1 mg of biotherapy should make tremendous effect. Patients not responding to this therapy may be given second set treatments. But, the second dosing will be delayed for a period of one month in order to eliminate the possibility of interference by antibodies which may develop against these proteins.

BRIEF DESCRIPTION OF THE DRAWINGS

Drawing No. 1.

High pressure liquid chromatography profile of *Crotalus atrox* venom using an anion exchange column. Peak no. 5 represents cancer cell inhibitor Atroporin and has the maximum cytolytic activity as shown in table 1.

Drawing No. 2.

High pressure liquid chromatography profile of *Naja n. kaouthia* venom using an anion exchange column. Peak no. 4 represents cancer cell inhibitor Kaotree and has the maximum cytolytic activity as shown in table 2.

Drawing No. 3.

High pressure liquid chromatography profile for the concentrate of fraction 5, of *Crotalus atrox* venom showing a single peak of pure cancer cell inhibitor Atroporin. Atroporin from fraction 5 was concentrated to 1/20 volume to increase its protein concentration to 5 mg/ml. Such concentrate was run through the HPLC to obtain 100% pure Atroporin.

Drawing No. 4.

High pressure liquid chromatography profile for the concentrate of fraction 4 of *Naja n. kaouthia* venom showing a single peak of pure cancer cell inhibitor, Kaotree. Kaotree from fraction 4 was concentrated to 1/20 volume to increase its protein concentration to 5 mg/ml. Such concentrate was run through the HPLC to obtain 100% pure Kaotree.

Drawing No. 5.

Electrophoretic profile of pure cancer cell inhibitors, Atroporin and Kaotree on 14% precast "Novex®" gel with markers. The molecular weights of Atroporin and Kaotree are approximately 35,000 and 6,000 daltons respectively.

Drawing Nos. 6A, 6B and 6C

National Cancer Institute data sheet for Atroporin showing various measures of effectiveness against cancer cell culture versus different cancer cell lines shown in column 1. This data is based on optical density measurements made before and after 48 hours of culture with and without the inoculum at various concentrations. GI50=conc. giving 50% Growth Inhibition; TGI=conc. giving Total Growth Inhibition; LC50=conc. giving 50% Cell Death. These concentrations are given as $\log_{10}$ (µg/ml). Low or negative LC50 is desirable. A value of >1.00 indicates LC50 out of range of concentrations studied. These findings are regarded as statistically significant and Atroporin is indicated for further study.

Drawing Nos. 7A, 7B and 7C

National Cancer Institute data sheet for Kaotree showing various measures of effectiveness against cancer cell culture versus different cancer cell lines shown in column 1. See explanation for drawing no 6. Kaotree also shows activity here, although not as much as Atroporin according to the routine statistical correlations used by NCI. Kaotree will be tested further. NCI may test Atroporin and Kaotree in animals.

DETAILED DESCRIPTION OF THE INVENTION

Cancer cell inhibitor Atroporin consists essentially of a peptide having the partial amino acid sequence given by SEQ ID: 1 and Kaotree has the sequence given by SEQ ID: 2. It is believed that any peptide having the partial amino acid sequence SEQ ID No: 1 or 2 exhibits substantial utility as a cancer cell inhibitor and will be a potent anti cancer agent, regardless whether it is synthesized or derived from natural sources. The term "cancer cell inhibitor" is understood to mean: a substance whose presence produces a substantial cytolytic effect on various types of cancer cells, wherein, the cytolytic effect is indicated, for example, by a vital staining and increased doubling time of surviving cells.

Preferably, the peptide cancer cell inhibitor Atroporin contains first fifteen N-terminal amino acids given by SEQ ID No: 1, and similarly for Kaotree the N-terminal sequence is given by SEQ ID No: 2 and the corresponding molecular weights are approximately 35,000 and 6,000 daltons as revealed by electrophoresis. In addition, the cancer cell inhibitors, Atroporin and Kaotree, are water soluble and stable at 4° C., which temperature maintains the biological activity. Atroporin and Kaotree are also stable at room temperature, 24° C., for several weeks and their anti cancer activity is unaltered by exposure to intense ultra violet light overnight.

Cancer cell inhibitors Atroporin and Kaotree may be obtained as fraction of venom, from any species of poisonous snake. In this invention Atroporin and Kaotree are preferably obtained from the venoms of *Crotalus atrox*, the Western diamondback rattle snake and *Naja n*. kaouthia, the Thailand cobra, respectively.

The active cancer cell inhibitors Atroporin and Kaotree may be obtained by collecting and separating the proper peptide fraction using either gel filtration chromatography, electrophoresis, high pressure liquid chromatography, ion exchange chromatography, capillary electrophoresis or other suitable method and combinations thereof.

Fractionation of Venom

The active cancer cell inhibitors are preferably separated from fresh fr

TABLE 2-continued

Cytolytic effect of various fractions of Naja n.kaouthia venom on mouse myeloma cancer cells.

| Fraction | Protein concentrations | | | | | |
|---|---|---|---|---|---|---|
| | 5 µg/ml | 2.5 µg/ml | 1 µg/ml | 0.5 µg/ml | .25 µg/ml | 0.1 µg/ml |
| 3 | + | + | + | − | − | − |
| 4* | + | + | + | + | + | + |
| 5 | + | + | − | − | − | − |
| 6 | + | + | − | − | − | − |
| 7 | + | + | + | − | − | − |

+ cells showing cytolytic effects
− cells look unaffected
*this is the anti cancer fraction Results show that fraction 5 of *Crotalus atrox* and fraction 4 of *Naja n. kaouthia* venoms are most cytolytically active to mouse myeloma cancer cells. Hence, fractions 5 of *Crotalus atrox* and 4 of *Naja n. kaouthia* are designated as cancer cell inhibitors in this art, which are further designated as Atroporin and Kaotree.

the other hand, Kaotree is more cytolytic to ZR-75, breast cancer cells, than Atroporin. The combination of Atroporin and Kaotree showed elevated cytolytic activity, for these human cancer cells, in comparison to either Atroporin or Kaotree alone. Atroporin and Kaotree are derived from different species, having different molecular weights, and

TABLE 3

Cytolytic Effects of Atroporin and Kaotree on Human Cancer Cells at various Concentrations

| Agent | Conc. µg/ml | Breast | | | Colon | | Ovary | Liver |
|---|---|---|---|---|---|---|---|---|
| | | HBL-100 | BT-20 | ZR-75-1 | HT-29 | Diji | Sk-ov-3 | CCL-13 |
| Atro-porin | 5.0 | + | + | + | + | + | + | + |
| | 2.5 | + | + | + | + | + | + | + |
| | 1.0 | + | + | + | + | + | + | + |
| | 0.5 | + | + | − | + | − | + | − |
| | 0.1 | − | − | − | − | − | − | − |
| Kao-tree | 5.0 | + | + | + | + | + | + | + |
| | 2.5 | + | + | + | + | + | + | + |
| | 1.0 | + | + | + | + | + | + | + |
| | 0.5 | + | + | + | + | − | − | − |
| | 0.1 | − | − | − | − | − | − | − |
| Atro-porin + Kao-tree | 5.0 | + | + | + | + | + | + | + |
| | 2.5 | + | + | + | + | + | + | + |
| | 1.0 | + | + | + | + | + | + | + |
| | 0.5 | + | + | + | + | − | + | − |
| | 0.1 | − | − | − | − | − | − | − |

+ 100% killing of cells
− partial or no killing

The cell lines used for this work were obtained from ATCC in Rockville, Md. The common names used in the table above have following ATCC designations:

| 1. | HBL-100 | cancer of breast | HBT 124 |
| 2. | BT-20 | cancer of breast | BT 474 |
| 3. | ZR-75-1 | cancer of breast | CRL 1500 |
| 4. | HT-29 | cancer of colon | HBT 38 |
| 5. | Diji | cancer of colon | M. D. Anderson |
| 6. | Sk-ov-3 | cancer of ovary | HTB 77 |
| 7. | CCL-13 | cancer of mouth | KB CCL17 |

The results of table 3 show that both Atroporin and Kaotree are cytolytic to variety of human cancer cell lines, in concentrations as low as 0.5 µg/ml. Atroporin is more cytolytic to Sk-ov-3, ovary cancer cells, than Kaotree. On are apparently complementing each other for cytolytic activity. Therefore, a combination of the two shows elevated activity for two cell lines. Atroporin and Kaotree together may provide a biotherapy for various types of cancers. Results show that venom derived cancer cell inhibitor is cytolytic to wide range of cancer cells. Therefore, cancer cell inhibitors like Atroporin and Kaotree can be excellent biotherapy for various types of cancers.

The cytolytic activity of cancer cell inhibitor was studied on wide range of animal cancer cells and primary culture cells from normal mouse, such as spleen, liver, kidney and red blood cells (RBCs—erythrocytes). The test results for cytolytic effect of cancer cell inhibitor on various types of established cancer cell lines and normal cells are shown in table 4.

TABLE 4

Effects of Atroporin and Kaotree on Normal and Cancer Animal Cells.

| Agent | conc. µg/ml | Primary cell cultures of normal mouse | | | | Animal cancer cells | | |
|---|---|---|---|---|---|---|---|---|
| | | Spleen | Liver | Kidney | RBCs | Mouse SP2 | Rat PC12 | Monkey Vero |
| Atro-porin | 5.0 | − | − | − | − | + | + | + |
| | 2.5 | − | − | − | − | + | + | − |
| | 1.0 | − | − | − | − | + | − | − |
| | 0.5 | − | − | − | − | + | − | − |
| | 0.1 | − | − | − | − | − | − | − |
| Kao-tree | 5.0 | − | − | − | − | + | + | + |
| | 2.5 | − | − | − | − | + | + | − |
| | 1.0 | − | − | − | − | + | − | − |
| | 0.5 | − | − | − | − | + | − | − |
| | 0.1 | − | − | − | − | + | − | − |
| Atro-porin + Kao-tree | 5.0 | − | − | − | − | + | + | + |
| | 2.5 | − | − | − | − | + | + | + |
| | 1.0 | − | − | − | − | + | − | − |
| | 0.5 | − | − | − | − | + | − | − |
| | 0.1 | − | − | − | − | + | − | − |

+ 100% killing of cells
− partial or no killing of cells

The results of table 4 clearly show that Atroporin and Kaotree alone or in combination have no cytolytic effect on normal mouse spleen, liver, kidney and erythrocytes cells in concentrations as high as 5 µg/ml which is 10 times higher than required to elicit cytolytic effect on cancer cells. These results are in good agreement with the findings of Garcia et al. (9), who observed greater than 40% inhibition of seven colon cancer cell lines and only 12% in normal colonic mucosa cells as an effect of an antibiotic herbimycin A. Kaotree is five times more cytolytic to mouse myeloma cells than Atroporin and the combination of two is as good as Kaotree alone, indicating that these two proteins complement each other for anti cancer activity.

The results were read after 48 hours incubation. Cut off point was taken to be 100% killing as established by microscopic examination. No quantitation was made for partial killing between 100% and 0%. Atroporin and Kaotree were tested by the National Cancer Institute (NCI) screening procedure and their results for most of the cell lines and, more specifically, for breast and colon cancer cells are in agreement. The NCI screening procedure is not strictly comparable because of differences in procedure, media etc. NCI does not test compounds on normal cells. The NCI data sheets are enclosed as Drawing No. 6 and drawing No. 7.

Animal In Vivo Experiments

1. Prevention of Ascitic Tumor Formation in Mice

Two million SP/2 mouse myeloma cells (ATCC 1581 CRL, Rockville, Md.) were injected intraperitoneally (IP) to produce ascites in 20, five to six week old, Balb/C mice. Injected mice were divided into four groups, 5 mice in each group. Starting on day 0, group I was given 0.2 ml PBS to serve as control. Group II was given 0.2 ml containing 5 µg of Atroporin, group III was given 5 µg of Kaotree and group IV was given 5 µg of combination of Atroporin and Kaotree for five consecutive days. Thus, each group received 25 µg of total protein. After 60–70 days mice in the control came down with ascites tumors and died in the next 10–20 days. All mice treated with Atroporin and Kaotree failed to develop bulging stomachs, i.e. ascitic tumors, and survived until the experiments were terminated. These experiments illustrate that tumor formation was prevented by treatment with Atroporin or Kaotree alone and also by the combination of both.

2. Regression of Ascitic Tumors in Mice

Two million SP/2 mouse myeloma cancer cells were injected IP into 20 Balb/C mice of 5–6 weeks age to produce ascitic tumors. When the mice started showing bulging stomachs, which was after 60 days, the mice were divided into four groups five of each. Mice in group I were given PBS to serve as controls. Mice in groups II and III were treated with Atroporin and Kaotree respectively. The mice in group IV were treated with the combination of Atroporin and Kaotree. In each case 5 µg of protein was administered for five consecutive days totaling 25 µg.

The mice in group I died in the next 10–20 days with ascitic tumors. None of the mice in group IV died. 60% and 80% mice of groups II and III respectively survived and of those which died, the incubation period was longer than the controls. These experiments prove that the treatment with Atroporin or Kaotree causes regression of ascitic tumors in mice; and the combination of Atroporin and Kaotree provided 100% which is better than either agent alone.

TABLE 5

Prevention and Regression of Ascitic Tumors in Mice by Atroporin and Kaotree Treatment

| Group | Prevention | Mortality | Regression | Survival |
|---|---|---|---|---|
| I. Control | 0/5 | 100% | 0/5 | 0 |
| II. Atroporin | 5/5 | 0 | 3/5 | 60% |
| III. Kaotree | 5/5 | 0 | 4/5 | 80% |
| IV. Atroporin + Kaotree | 5/5 | 0 | 5/5 | 100% |

Note that 100% regression of partially developed ascitic tumors occurred with 25 µg of the combination biotherapy consisting of an equal mixture of Atroporin and Kaotree, which is substantially better than for either of them alone.

Cell culture experiments show that $10^5$ cells of various cancers are killed by incorporating 0.5 µg/ml of Atroporin or Kaotree. In the mouse experiments, two million cells were injected, which is 20 times greater, and in theory should require 10 µg to get a similar effect. But in vitro and in vivo systems can not be compared in strict sense. Therefore, 25 μg were used arbitrarily for these mouse studies.

Suggested Strategy for Human Treatment

Based on the findings from cell culture and mouse experiments we suggest the following strategy for human treatment.

In humans, depending upon the cancerous state of the patient, the combination of Atroporin and Kaotree consisting of 200 μg/ml will be administered intravenously or by direct perfusion or other suitable means of contacting the cancer cells, as follows:

| Day 1 | 200 μg | 1 ml |
| Day 2 | 400 μg | 2 ml |
| Day 3 | 400 μg | 2 ml |

Thus, the first set of treatments will consist of 1 mg in total. This quantity seems to be terribly low in comparison to the chemotherapeutic drugs currently in practice. However, based on cell culture and mouse experiments 1 mg of Atroporin or Kaotree or the combination of both should kill from 80 to 200 million cancer cells. Alternatively, the dosage could be increased to 500 μg per day for five consecutive days. Our experience tells us that by our unique methodology venom derived proteins are more biologically active than obtained by other methods.

We suggest that for safety the following tests to be performed before the first set of treatments and again one month after.

(1) Total white blood cell count (2) Total platelet count

We believe that 1 mg of biotherapy should make tremendous effect. Patients not responding to this therapy may be given second set treatments, but the second dosing will be delayed for a period of one month in order to eliminate the possibility of interference by antibodies.

Analysis of Cancer Cell Inhibitor Active Peptides

Figure 1:
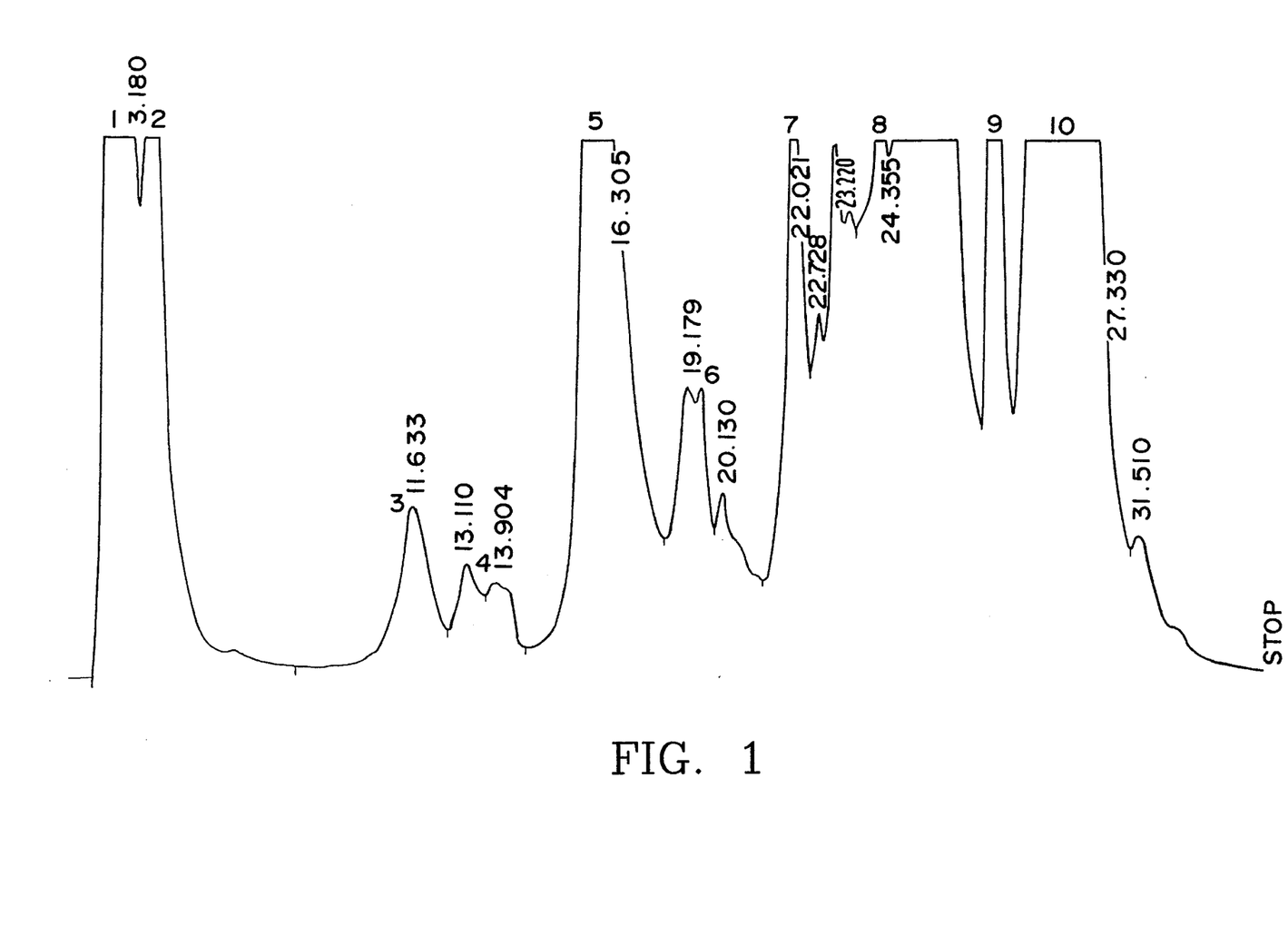
Figure 2:
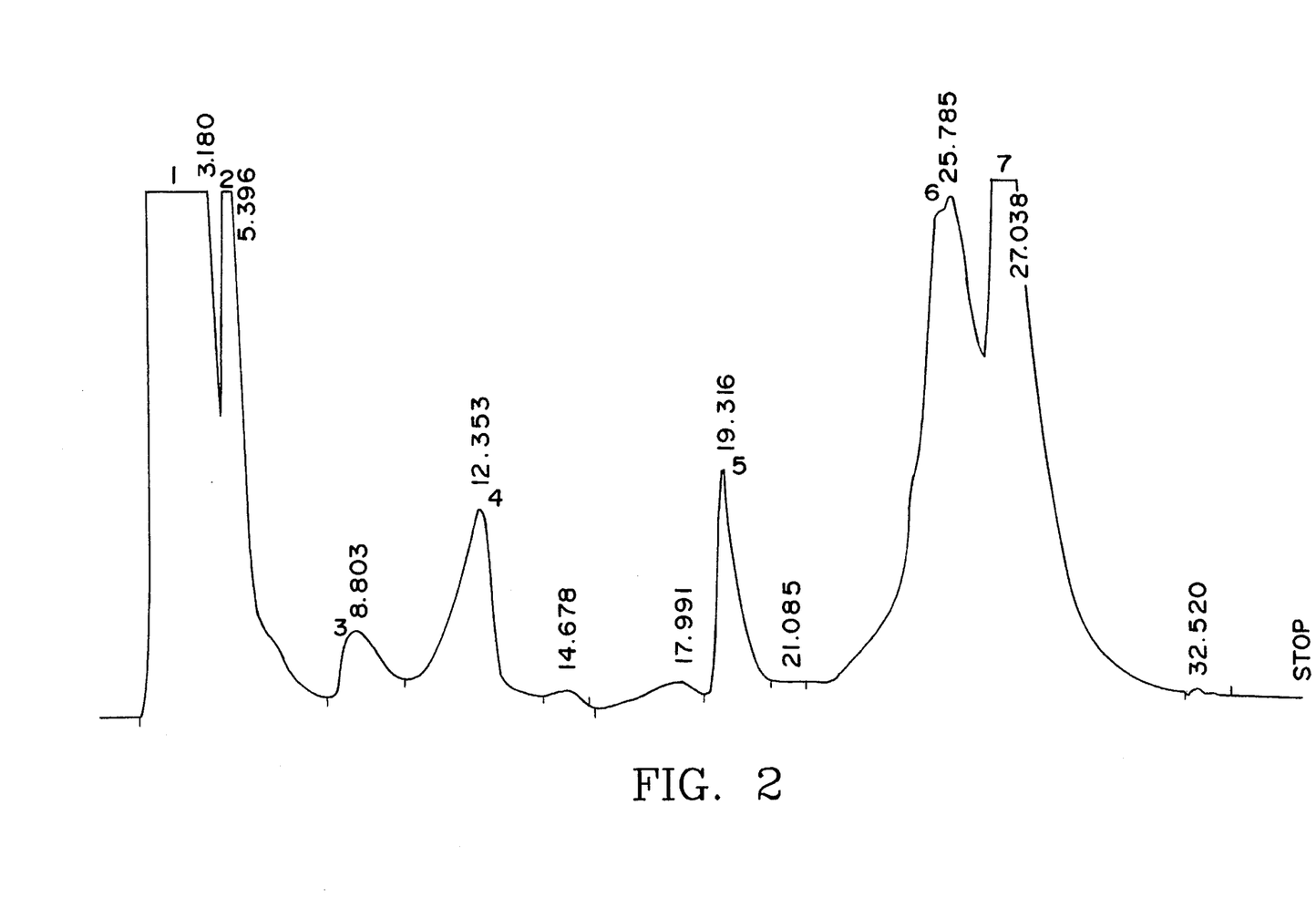
Figure 3:
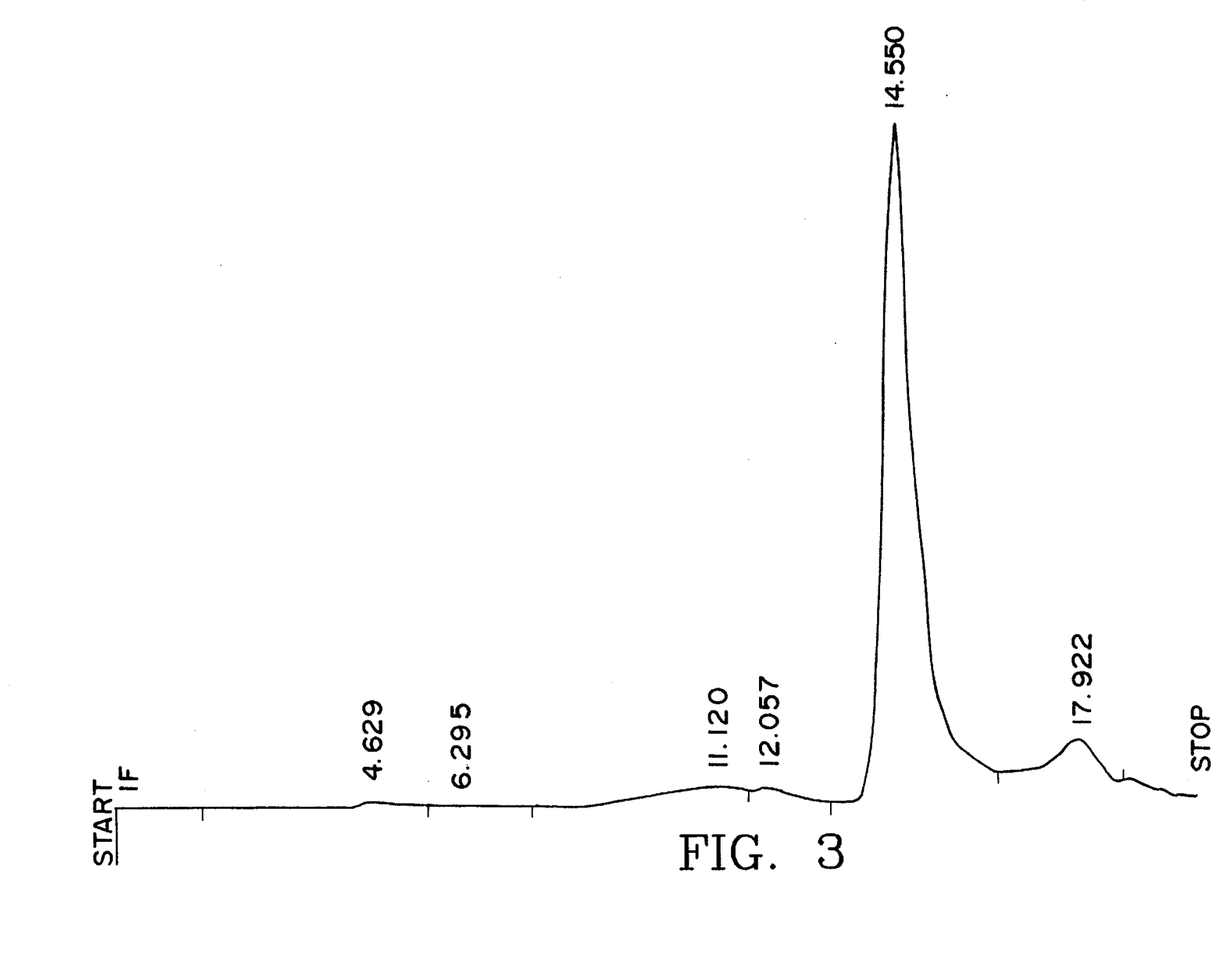
Figure 4:
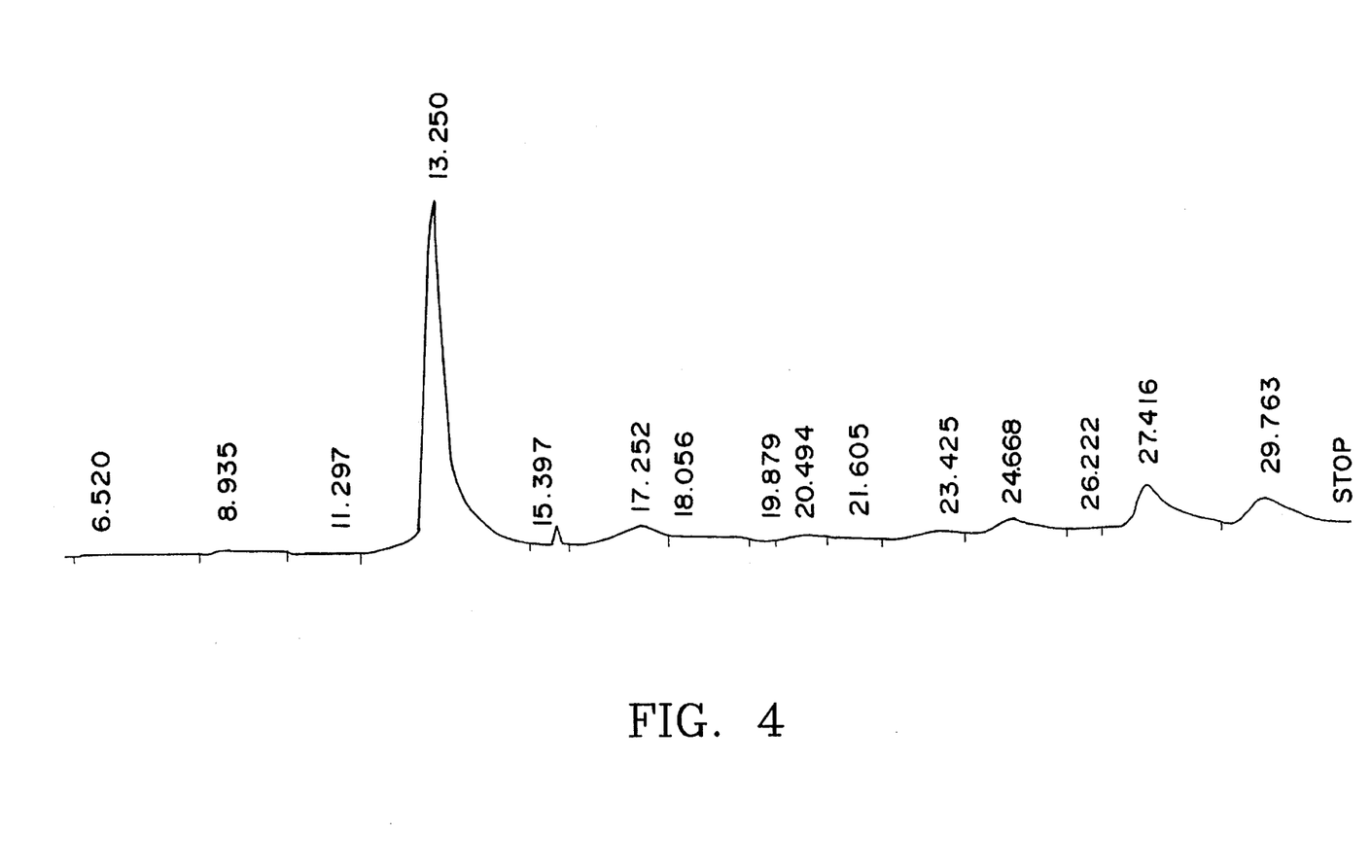
Figure 5:
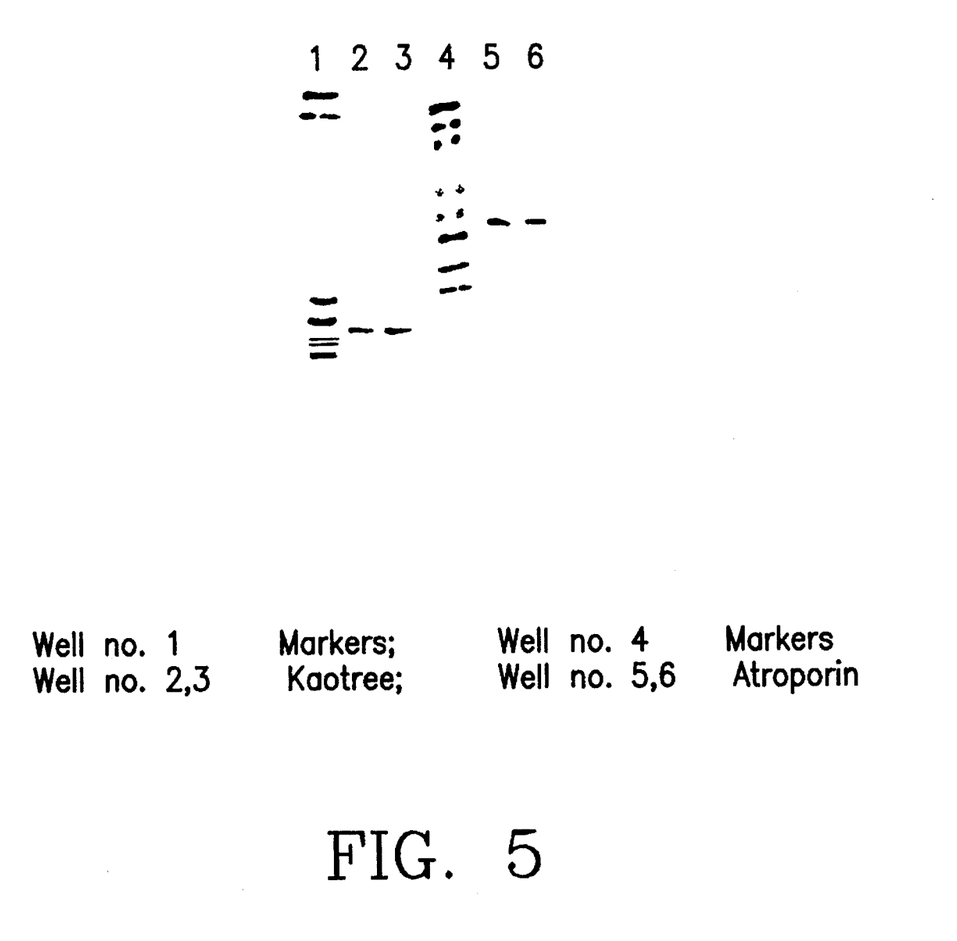
Figure 6A:
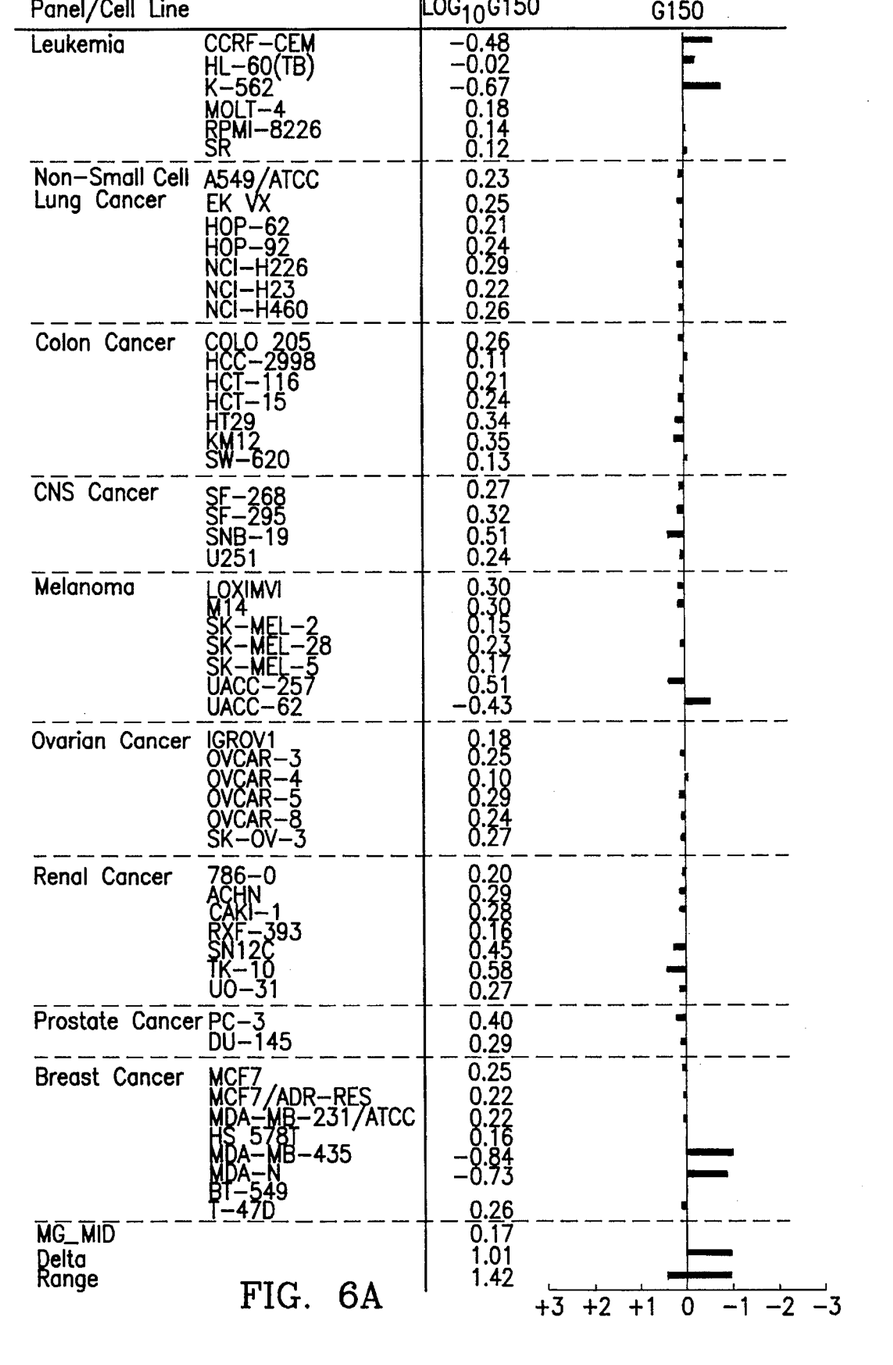
Figure 6B:
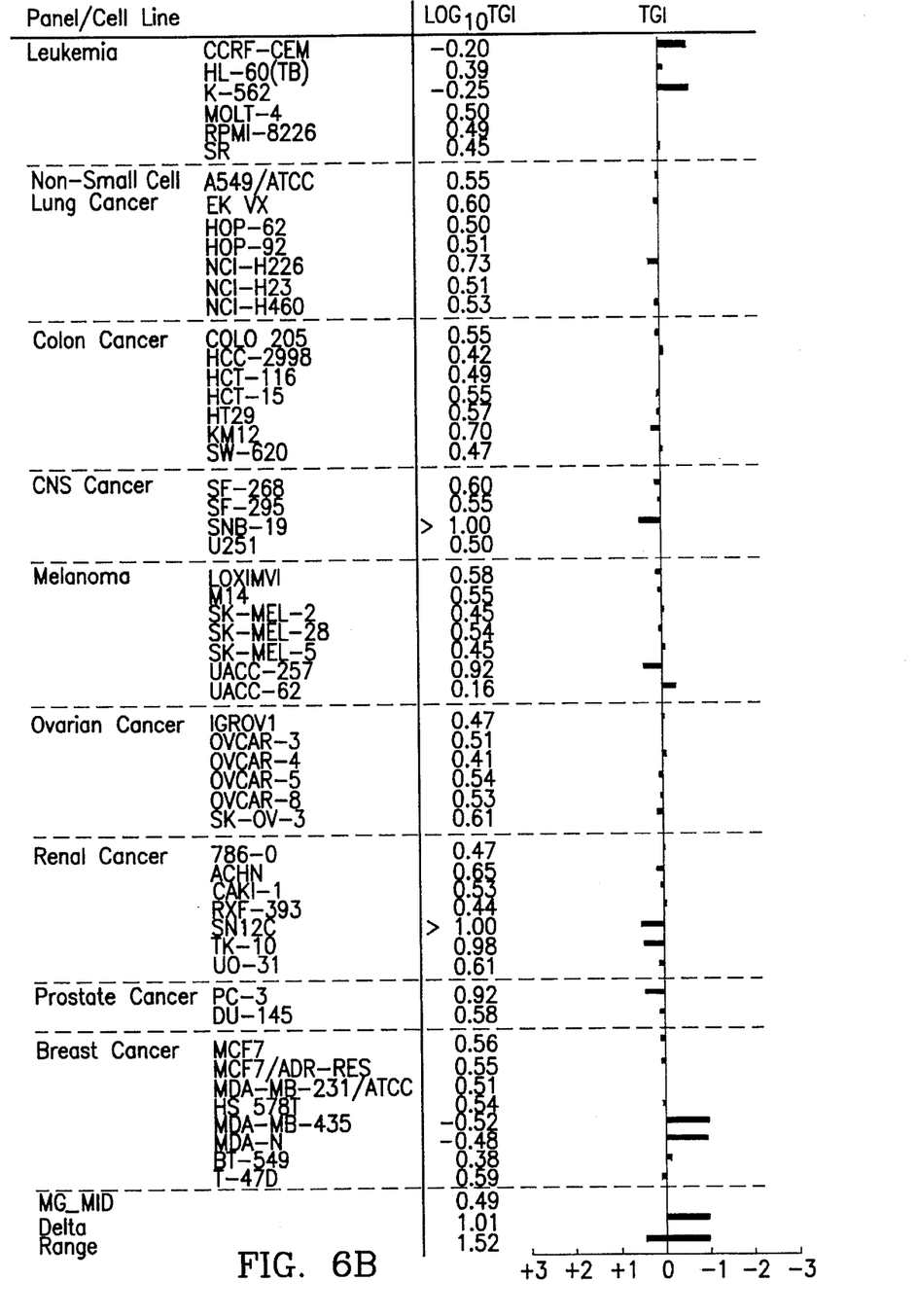
Figure 6C:
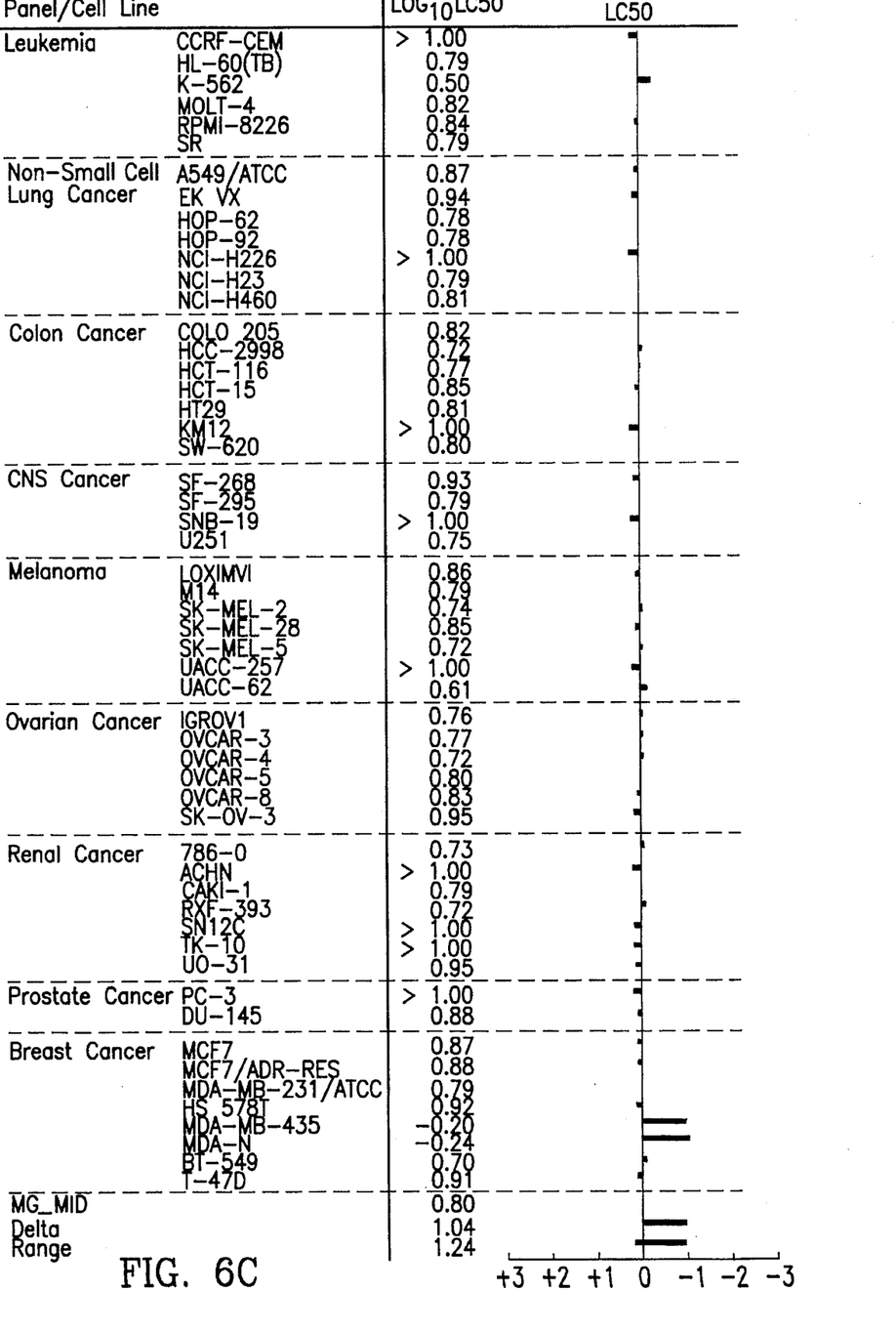
Figure 7A:
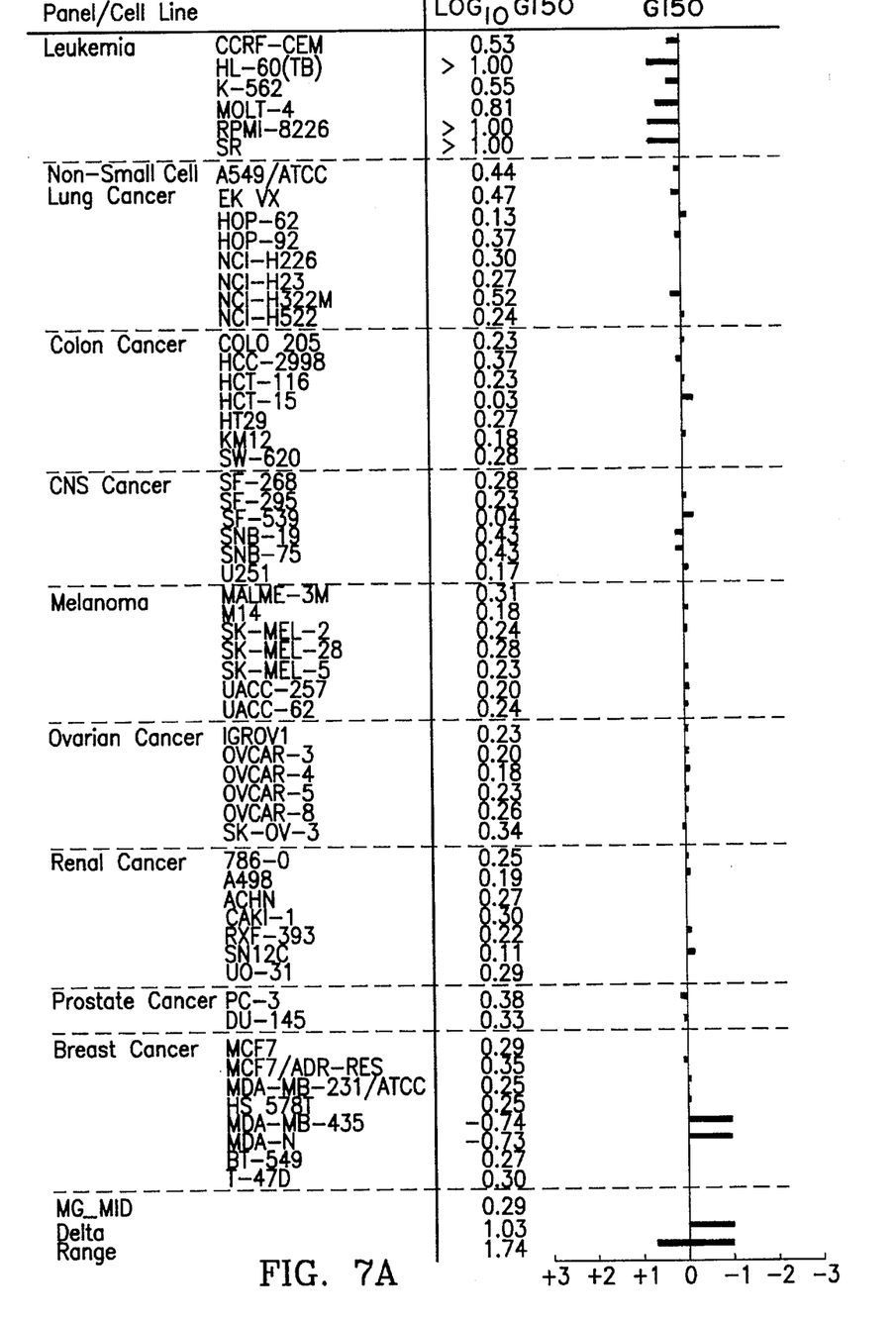
Figure 7B:
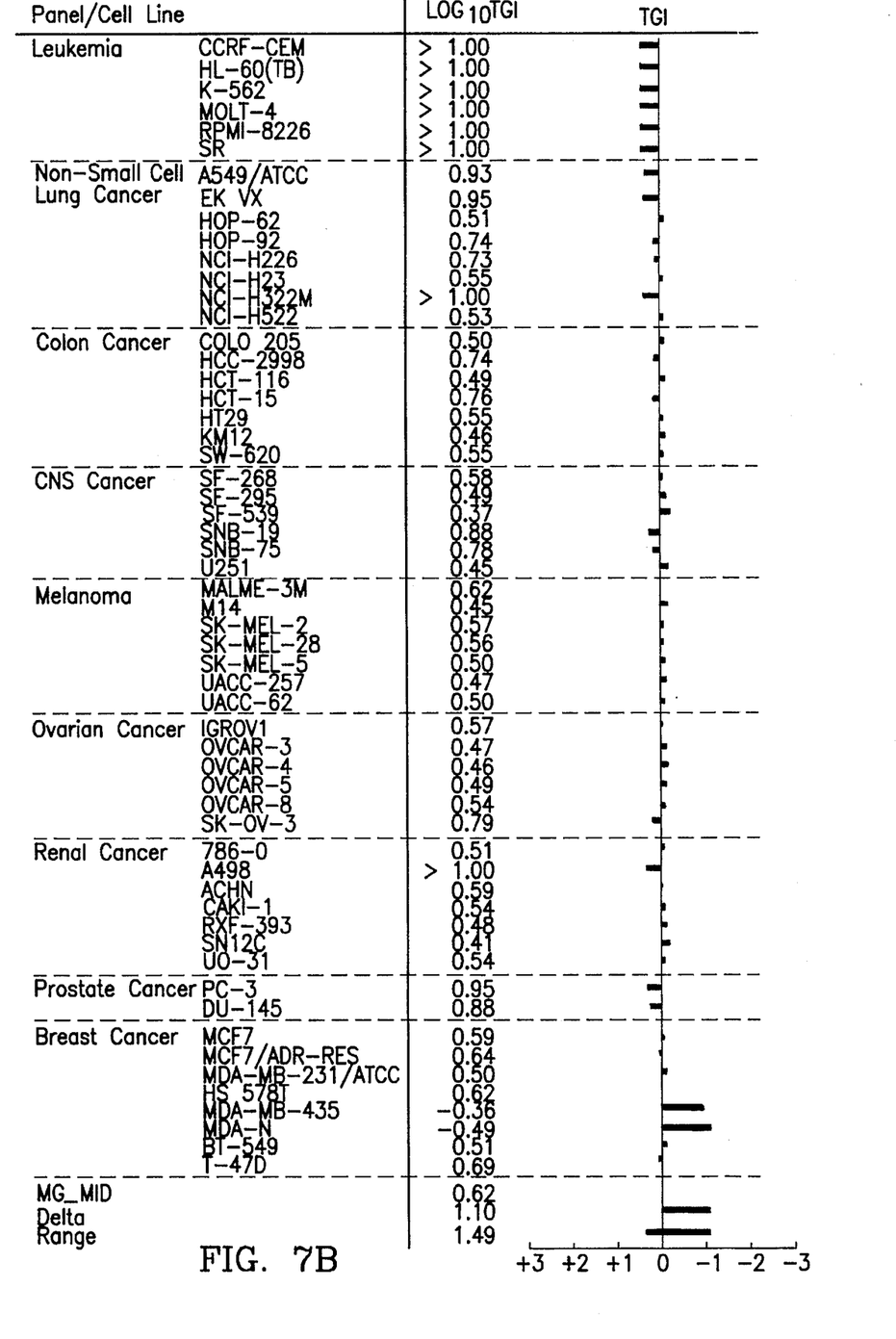
Figure 7C:
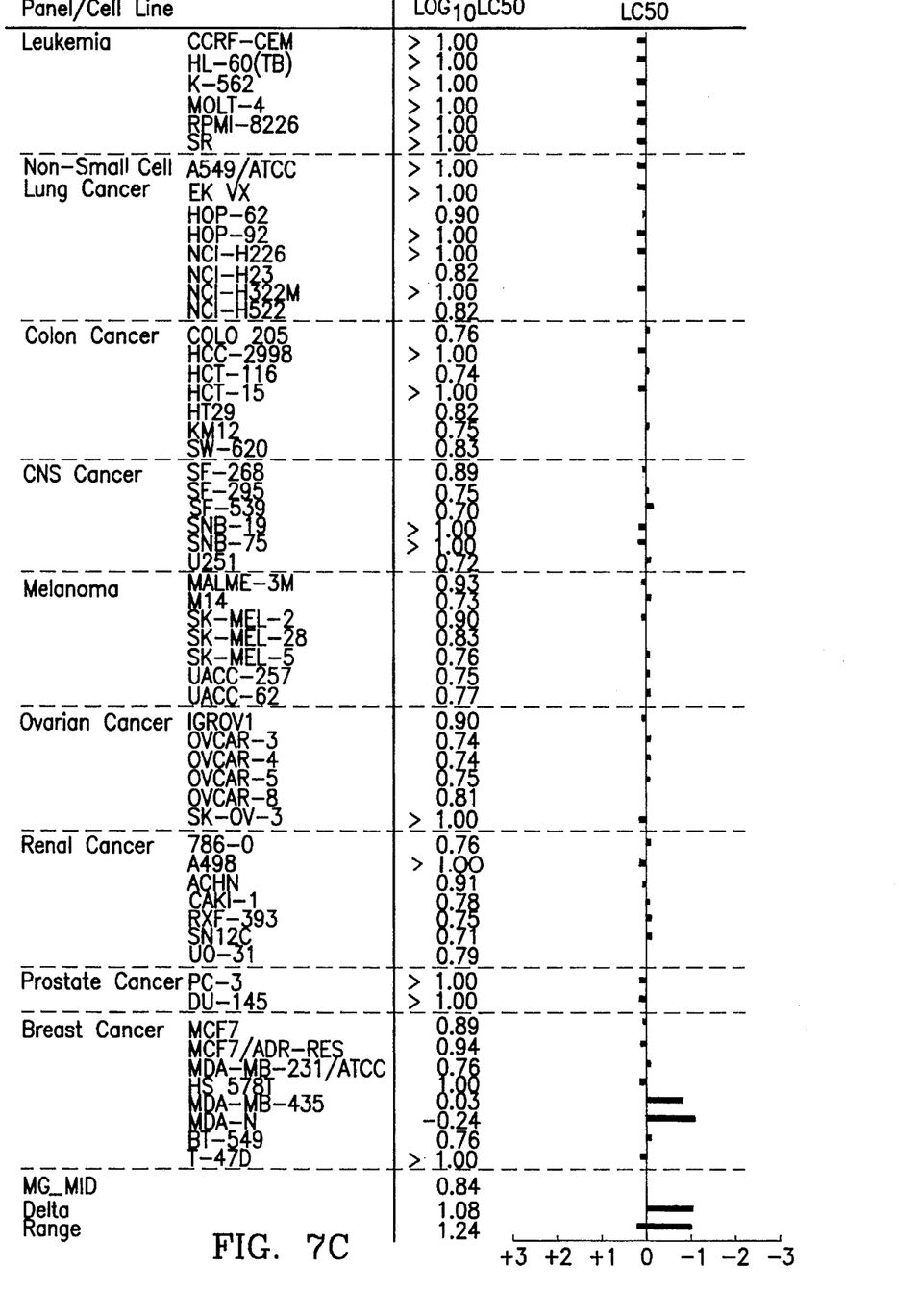

The concentrated fraction 5 of *Crotalus atrox* and fraction 4 of *Naja n. kaouthia*, which were obtained by fractionating the crude venoms, and which resolved into a single peak after a second passage on high pressure liquid chromatograph under identical conditions. The peak materials were estimated to have a molecular weight in the vicinity of 35,000 and 6,000 daltons, when compared with "Novex®" markers aprotinin, lysozyme, carbonic anhydrase and bovine serum albumin having molecular weights 6,000, 14,400, 31,000 and 66,000 daltons respectively on 14% precast gel (Drawing no. 5).

Cancer cell inhibitors, Atroporin and Kaotree, were analyzed for amino acid composition and the results are seen in table 6.

TABLE 6

| Amino Acid Composition | | |
|---|---|---|
| Amino acid | Atroporin mole % | Kaotree mole % |
| Aspartic acid | 11.46 | 10.51 |
| Glutamic acid | 7.01 | 8.87 |
| Serine | 7.54 | 8.02 |
| Glycine | 9.01 | 6.72 |
| Histidine | 2.23 | 3.14 |
| Arginine | 4.04 | 1.90 |
| Threoine | 6.55 | 7.88 |
| Alanine | 6.04 | 3.56 |
| Preline | 6.59 | 4.99 |
| Tyrosine | 2.81 | 3.05 |
| Valine | 5.64 | 4.12 |
| Methionine | 1.98 | 3.81 |
| Cysteine | 6.44 | 17.52 |
| Isoleucine | 5.39 | 1.03 |
| Leucine | 6.79 | 1.71 |
| Phenylalanine | 3.79 | 6.68 |
| Lysine | 6.69 | 6.50 |

The amino acid sequence of the peptide was determined using the material of the single peak, obtained from the second passage through high pressure liquid chromatography. The partial sequences for the first fifteen amino acids from N-terminal is SEQ ID No: 1 and 2.

The forgoing description of the invention is illustrative and explanatory thereof, and many variations will occur to those in the art. It is intended that all such variations within the scope and spirit of the appended claims be embraced thereby.

We claim:

1. A method for treating a patient having a cancer tumor, said tumor comprising a plurality of cancer cells, said method comprising contacting the plurality of cancer cells with molecules of Atroporin at a dosage level sufficient to slow or regress the cancer tumor without significant destruction of normal cells which may also be contacted by Atroporin, wherein said Atroporin consists essentially of a single purified fraction obtained from snake venom, said fraction containing a single peptide having its first fifteen N-terminal amino acids as given by SEQ ID No: 1 and a molecular weight of about 35,000 Daltons.

2. A method for treating a patient having a cancer tumor said tumor comprising a plurality of cancer cells, said method comprising contacting the plurality of cancer cells with a combination of Atroporin and Kaotree so as to slow or regress the cancer tumor without significant destruction of normal cells which may also be contacted by molecules of Atroporin and Kaotree, wherein said Atroporin consists essentially of a single purified fraction obtained from snake venom, said fraction containing a peptide having its first fifteen N-terminal amino acids as given by SEQ ID No: 1 and a molecular weight of about 35,000 Daltons and said Kaotree consists essentially of a single purified fraction obtained from snake venom, said fraction containing a single peptide having its first fifteen N-terminal amino acids as given by SEQ ID No: 2 and a molecular weight of about 6,000 Daltons.

3. A method for treating a patient having a cancer tumor comprising a plurality of cancer cells, said method comprising contacting the plurality of cancer cells with molecules of Kaotree so as to slow or regress the cancer tumor without significant destruction of normal cells which may also be contacted by molecules of Kaotree, wherein said Kaotree consists essentially of a single purified fraction obtained from snake venom, said fraction containing a single peptide having its first fifteen N-terminal amino acids as given by SEQ ID No: 2 and a molecular weight of about 6,000 Daltons.

4. A method as in claim 3, wherein said snake venom is from the species *Naja n. kaouthia*.

* * * * *